US010029254B2

(12) United States Patent
Mastromatteo et al.

(10) Patent No.: US 10,029,254 B2
(45) Date of Patent: Jul. 24, 2018

(54) DEVICE AND METHOD OF DETECTING TSH

(71) Applicant: STMicroelectronics S.r.l., Agrate Brianza (IT)

(72) Inventors: Ubaldo Mastromatteo, Bareggio (IT); Gabriele Barlocchi, Cornaredo (IT); Flavio Francesco Villa, Milan (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 392 days.

(21) Appl. No.: 14/869,718

(22) Filed: Sep. 29, 2015

(65) Prior Publication Data
US 2016/0016168 A1  Jan. 21, 2016

Related U.S. Application Data

(62) Division of application No. 13/621,176, filed on Sep. 15, 2012, now Pat. No. 9,170,183.

(30) Foreign Application Priority Data

Sep. 23, 2011  (IT) .............................. TO2011A0854

(51) Int. Cl.
*G01N 5/02*  (2006.01)
*B01L 3/00*  (2006.01)
(Continued)

(52) U.S. Cl.
CPC .......... *B01L 3/502715* (2013.01); *G01N 5/02* (2013.01); *G01N 33/5438* (2013.01);
(Continued)

(58) Field of Classification Search
None
See application file for complete search history.

(56) References Cited

U.S. PATENT DOCUMENTS 6,196,059 B1  3/2001  Kosslinger et al.
2003/0162304 A1  8/2003  Dority et al.
(Continued)

FOREIGN PATENT DOCUMENTS

EP  2 204 641 A1  7/2010
WO  2004/001392 A1  12/2003
(Continued)

OTHER PUBLICATIONS

Italian Search Report, dated Mar. 6, 2012, for Italian Application No. TO20110854, 9 pages.
Tuantranont et al., "A review of monolithic multichannel quartz crystal microbalance: A review," *Analytica Chimica Acta* 687:114-128, 2011.

*Primary Examiner* — Rebecca L Martinez
(74) *Attorney, Agent, or Firm* — Seed IP Law Group LLP

(57) ABSTRACT

A device for detecting the concentration of biological materials is formed in a body having a plurality of fluidic paths connectable to a multi-microbalance structure carrying a plurality of microbalances, each microbalance having a sensitive portion facing a reaction chamber. The body and the multi-microbalance structure are configured to be mechanically coupled together and each microbalance is configured to be coupled to a respective fluidic path. Each fluidic path includes an inlet, a duct and a liquid waste, each duct being configured to be coupled with a respective reaction chamber. The plurality of fluidic paths and microbalances form at least one first and one second reference cells and one first sample cell.

20 Claims, 8 Drawing Sheets

(51) Int. Cl.
*G01N 33/543* (2006.01)
*G01N 33/76* (2006.01)
G01N 29/02 (2006.01)
G01N 35/00 (2006.01)

(52) U.S. Cl.
CPC ....... *G01N 33/54366* (2013.01); *G01N 33/76* (2013.01); *B01L 2200/025* (2013.01); *B01L 2200/027* (2013.01); *B01L 2200/028* (2013.01); *B01L 2200/0684* (2013.01); *B01L 2300/0645* (2013.01); *B01L 2300/087* (2013.01); *B01L 2400/049* (2013.01); *G01N 29/022* (2013.01); *G01N 2035/00237* (2013.01)

(56) References Cited

U.S. PATENT DOCUMENTS

| | | |
|---|---|---|
| 2004/0093947 A1 | 5/2004 | Brederlow et al. |
| 2007/0016378 A1 | 1/2007 | Andersson |
| 2007/0172940 A9 | 7/2007 | Manalis et al. |
| 2008/0034840 A1 | 2/2008 | Mutharasan et al. |
| 2008/0156100 A1 | 7/2008 | Hines |
| 2008/0204043 A1 | 8/2008 | Wang et al. |
| 2009/0088982 A1 | 4/2009 | Fukushima et al. |
| 2010/0075347 A1 | 3/2010 | Daseratha et al. |
| 2010/0170324 A1 | 7/2010 | Mastromatteo et al. |

FOREIGN PATENT DOCUMENTS

| | | |
|---|---|---|
| WO | 2006/047760 A1 | 5/2006 |
| WO | 2009/136892 A1 | 11/2009 |

DEVICE AND METHOD OF DETECTING TSH

BACKGROUND

Technical Field

The present invention relates to PCR devices for biological analysis.

Description of the Related Art

The present invention relates to a device and method for detecting the concentration of biological materials, in particular a TSH (Thyroid Stimulating Hormone), in a sample.

Typical procedures for analyzing biological materials, such as nucleic acid, protein, lipid, carbohydrate, and other biological molecules, involve a variety of operations starting from raw material. These operations may include various degrees of cell separation or purification, cell lysis, amplification or purification, and analysis of the resulting amplification or purification products.

As an example, in DNA-based blood analyses, samples are often purified by filtration, centrifugation or electrophoresis so as to eliminate all the non-nucleated cells, which are generally not useful for DNA analysis. Then, the remaining white blood cells are broken up or lysed using chemical, thermal or biochemical means in order to liberate the DNA to be analyzed. Next, the DNA is denatured by thermal, biochemical or chemical processes and amplified by an amplification reaction, such as PCR (polymerase chain reaction), LCR (ligase chain reaction), SDA (strand displacement amplification), TMA (transcription-mediated amplification), RCA (rolling circle amplification), and the like. The amplification step allows the operator to avoid purification of the DNA being studied because the amplified product greatly exceeds the starting DNA in the sample.

If RNA is to be analyzed the procedures are similar, but more emphasis is placed on purification or other means to protect the labile RNA molecule. RNA is usually copied into DNA (cDNA) and then the analysis proceeds as described for DNA.

Finally, the amplification product undergoes some type of analysis, usually based on sequence or size or some combination thereof. In an analysis by microarray hybridization, for example, the amplified DNA is passed over a plurality of detectors made up of individual oligonucleotide detector fragments that are anchored, for example, on electrodes. If the amplified DNA strands are complementary to the oligonucleotide detectors or probes, stable bonds will be formed between them (hybridization) under specific temperature conditions. The hybridized detectors can be read by observation using a wide variety of means, including optical, electromagnetic, electromechanical or thermal means.

Other biological molecules are analyzed in a similar way, but typically molecule purification is substituted for amplification, and detection methods vary according to the molecule being detected. For example, a common diagnostic involves the detection of a specific protein by binding to its antibody. Such analysis requires various degrees of cell separation, lysis, purification and product analysis by antibody binding, which itself can be detected in a number of ways. Lipids, carbohydrates, drugs and small molecules from biological fluids are processed in similar ways.

Today, immunoassays of all kinds dominate the in vitro diagnostic (IVD) market. In 2005, according to Kalorama Information (New York City), the global immunoassay market generated 5.8 billion US$ in total revenues. New growth in immunoassays is tied to the development of autoimmune, cardiac, and tumor markers that play a significant role in disease diagnosis and monitoring. By 2010, the immunoassay market is expected to reach 8.1 billion US$ with an annual growth rate of 7%.

In the following, reference will be made to the measure of proteins/carbohydrates in a biological liquid, typically serum or urine, in biochemical tests called immunoassays that use the reaction of the proteins/carbohydrates to one or more antibodies as a basis for the assay measurement.

More particularly, in the following reference will be made to the measure of the concentration of the Thyroid Stimulating Hormone (TSH), but similar considerations and same methods and apparatuses apply to a variety of biological assays, e.g., for the measure of glycosylated hemoglobin and carbohydrate deficient transferrin (CDT) (the latter test being usable to discriminate between occasional and chronic drinking).

As known, the thyroid gland produces hormones that control the rate of metabolism and affect the development and operability of many other body functions. The two most common thyroid disorders are hyperthyroidism (overactive thyroid) and hypothyroidism (under active thyroid). Thyroid stimulating hormone (TSH) produced by the anterior pituitary gland regulates the production of two hormones (T3-triiodothyronine and T4-thyroxine) from the thyroid in a negative feedback mechanism. When levels of T3 and T4 are low, TSH is stimulated to produce more and more T3 and T4. Similarly, when levels are high, TSH production is decreased, which in turn decreases T4 and T3 levels.

In the past, the measure of the concentration of TSH was made using a first generation radio-immunological assay that had quite low sensitivity and was not able to discriminate low values, still within in the normal range, from slightly lower ones, correlating with hyperthyroidism.

Around the mid-eighties, second generation immunologic techniques were developed that used two anti-TSH antibodies, and the dual antibody system had somewhat improved the sensitivity. Later, in the nineties, these techniques were again improved to arrive at third generation methods that have a much higher sensitivity and allow the measure of TSH also for patients having serologic atypias tied to different thyroid diseases. Third generation TSH tests are solid phase enzyme-linked immunosorbent assays, using a mouse monoclonal anti-TSH antibody for solid phase immobilization and goat anti-TSH antibody linked to usually horseradish peroxidase, thus allowing signal amplification.

Third generation methods have a functional sensitivity (meaning therewith the lowest concentration allowing the dosage to maintain a dosage variation coefficient of about 20% or less) of about 0.01 to 0.02 µIU/mL and thus are able to provide quite precise results for hyperthyroid patients.

Traditional immunoassays, such as, e.g., ELISA (Enzyme-Linked ImmunoSorbent Assay) are based on the use of primary antibodies, together with enzymatic second antibodies and associated substrates to generate a final signal that may be compared with known thresholds.

These known solutions are fully manual, in that they require manual insertion of the samples, antibodies, and washing liquids and require an optical reader; in addition they require skilled personnel to perform the various binding and washing steps, so that they only allow clinical testing in central laboratories. In addition, they are complex, involve time-consuming procedures, and use potentially hazard and expensive materials.

BRIEF SUMMARY

One object of the invention is to provide a device and a method that allow detection of target biological materials, and that is simple, reproducible and reliable enough to be used in the field or in point-of-care settings, such as patient clinics, drugstores, mall kiosks, and the like.

According to the present invention, an apparatus and a method for detecting the concentration of biological materials are provided, as claimed in claims 1 and 12, respectively.

We have exemplified the device herein by testing TSH, an important thyroid hormone. However, any target for which sensitive antibodies are available can be measured using the device of the invention. Furthermore, changing the antibody to a nucleic acid will allow the detection of complementary nucleic acids, and thus, the device has wide applicability.

BRIEF DESCRIPTION OF THE DRAWINGS

For the understanding of the present invention, an embodiment thereof will be now described, purely as non-limitative example, with reference to the drawings, wherein.

DETAILED DESCRIPTION

Figure 1:
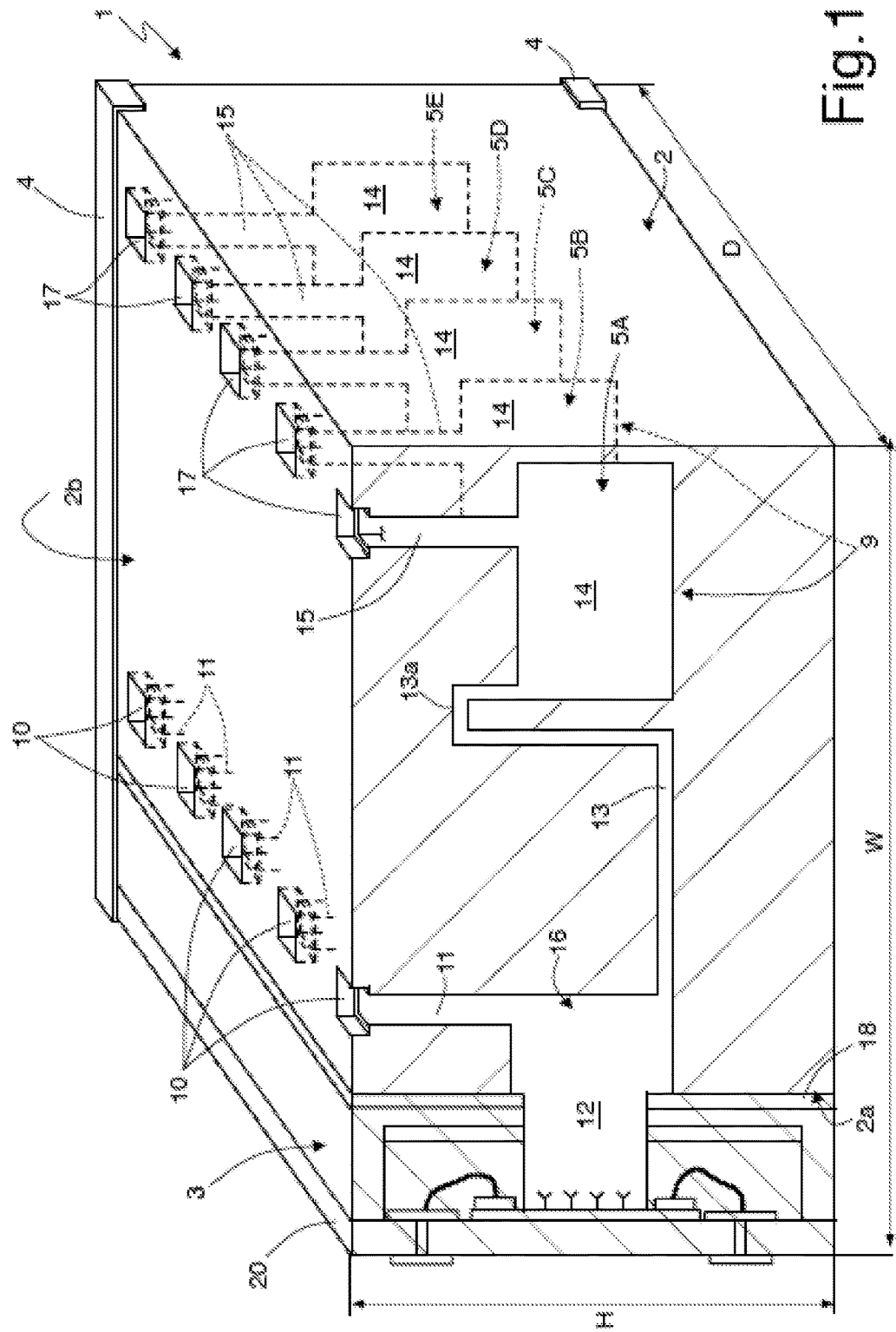
FIG. 1 is a perspective, partially cut view of a biochemical analysis device for detecting the concentration of biological materials, according to an embodiment.
Figure 2:
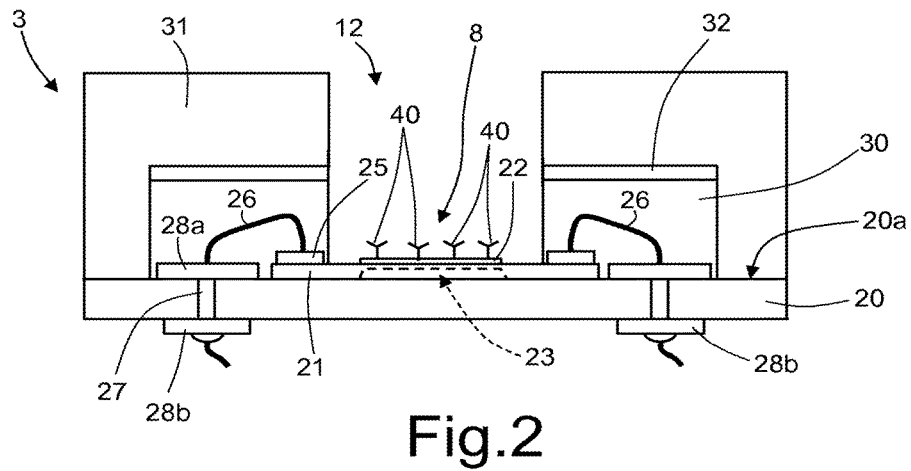
FIG. 2 is an enlarged cross-section of a portion of the device of FIG. 1.
Figure 3:
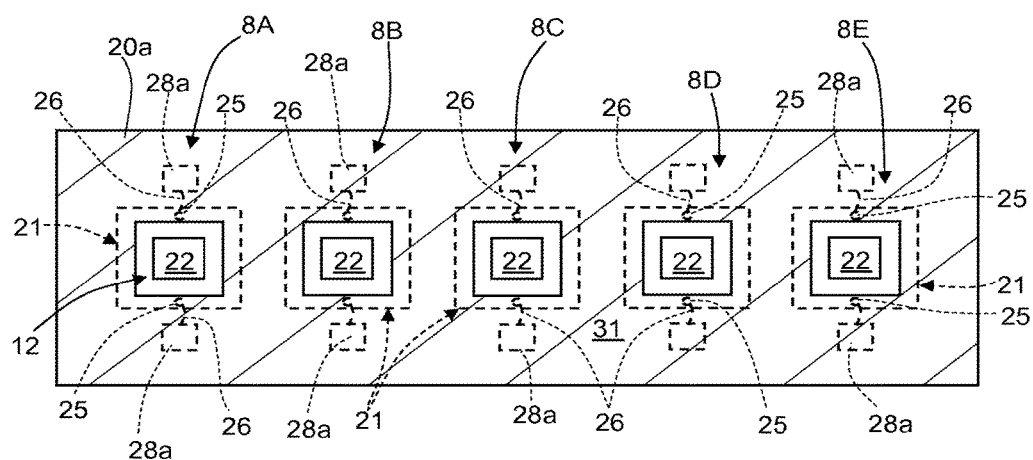
FIG. 3 is a top view of the portion of FIG. 2.

With reference to FIGS. 1-3, a concentration detecting device 1, of a disposable type, comprises a body 2, for example a plastic molded body, and a multi-microbalance structure 3 connectable to the body 2 by means of clips 4.

The body 2 has a plurality of fluidic paths 9 (here shown are five) that have the same structure (only one completely visible in FIG. 1), extend side-by-side to each other, and are each fluidically connectable to its own microbalance 8 of the multi-microbalance structure 3, so as to define five cells 5A-5E to be loaded with different samples, as explained hereinafter. The body 2 may be a parallelepiped or box of molded plastics, and have for example overall dimensions of $2 \times 5 \times 1.5$ cm$^3$ (W×D×H).

Each fluidic path 9 includes an inlet hole 10; a venting hole 17; an inlet conduit 11; a discharge conduit 13; a waste chamber 14; and a pumping conduit 15. In detail, each discharge conduit 13 extends from the respective inlet hole 10 and a respective reaction cavity 16 facing a respective reaction chamber 12 formed in a respective microbalance 8. Each discharge conduit 13 extends within the body 2 from the respective reaction portion 16 and the respective waste chamber 14 and has a winding shape with some portions extending on a lower level than other portions; and each pumping conduit 15 extends between the respective waste chamber 14 and the respective venting hole 17.

In some embodiments, the conduit has a portion 13a that is higher than the respective waste chamber 14 (and chambers 12 and 16); thus the fluids must be actively pumped over this gravity hill in order to reach the waste chamber 14. This feature protects against back flow from the waste chamber, and also serves to minimize contamination.

In an embodiment, holes 10, 17, conduits 11, 13, 15 and chambers 12, 14 of a same fluidic path are arranged generally coplanar and have a thickness (parallel to dimension D) of about 0.5-0.8 cm.

The body 2 may include a first face 2a connectable with the multi-microbalance structure 3 and a second face 2b, contiguous with and extending generally perpendicularly to the first face 2a. The second face 2b is intended, in use, to be a top face of the concentration detecting device 1, as will be clear hereinafter.

The inlet holes 10 are formed on the second or top face 2b and the inlet conduits 11 extend generally downwardly to the reaction cavities 16. The reaction cavities 16 open on the first face 2a of the body 2 to the respective reaction chambers 12 formed in multi-microbalance structure 3.

The venting holes 17 extend through the second face 2b, as well. An intermediate sealing layer 18, e.g., of biocompatible rubber, polyurethane, silicone or glue, is arranged between the body 2 and the multi-microbalance structure 3.

The multi-microbalance structure 3 (shown more in detail in FIG. 2) comprises a substrate 20, for example a plastic board of the type used for printed circuits. The substrate 20 has a first face 20a looking to or facing the body 2 and carrying the plurality of microbalances 8 (one for each measuring cell 5, as indicated above).

Each microbalance 8 may have the structure described in US 2010/0170324 and may include a die 21, of semiconductor material, e.g., of silicon, comprising a diaphragm 23 carrying a stack 22 of layers comprising a piezoelectric layer (not shown) sandwiched between a pair of electrodes (also not shown) and a sensitive layer (also not shown) able to bind with target chemicals.

Each die 21 may have an area of $200 \times 200$ or $300 \times 300$ $\mu m^2$. The stack 22 is connected to an oscillator (integrated in the same die or external to the die) to form a resonator, whose frequency depends on the mass of the microbalance, as explained in detail in above referenced US 2010/0170324 and shown schematically in FIG. 10. Thus, the binding of target chemicals can be detected from the change of frequency of the microbalances 8. However, other type of microbalances may be used.

The die 21 has pads 25 connected, through wires 26 and through connections 27 and first and second pads 28a, 28b, to a second face 20b of the substrate, for connection to the exterior.

A covering layer 30, for example of glob top, or other bio-compatible resin used in PCBs to cover chips, extends on the first face 20a of the substrate 20 except for at the stacks 22 and incorporates the wires 26. A transparent layer 31 (e.g., of glass or plastics) encloses the covering layer 30 and has windows or openings at the reaction chambers 12. The transparent layer 31 is attached to the body 2 through the intermediate sealing layer 18. A balance sealing layer 32 is sandwiched between the transparent layer 31 and the covering layer 30. The openings or cavities in the covering layer 30, the transparent layer 31 and the balance sealing layer 32 form the reaction chambers 12 (see also FIG. 3). As a whole, each reaction chamber 12 is preferably able to accommodate at least 20 µl of a liquid to be analyzed.

As indicated, the cells 5A-5E are intended to be loaded with different samples so as to define a calibration cell 5A, a first reference cell 5B, a second reference cell 5C, a first measure cell 5D and a second measure cell 5E, in cooperation with respective microbalances 8, thus also referred to as a calibration microbalance 8A, a first reference microbalance 8B, a second reference microbalance 8C, a first measure microbalance 8D and a second measure microbalance 8E.

Of course, the samples may be prepared in duplicate or triplicate for increased accuracy, and the cell numbers must be adjusted accordingly. Further, multiple calibration cells may be needed to prepare a standard curve. However, these five cells can demonstrate the basic precepts of the measuring device.

The method for measuring the concentration of the TSH hormone will be now described, with reference to FIGS. 4-9. In particular, FIGS. 4-7 show the supply of each cells 5A-5E in subsequent steps of the present method.

Figure 9:
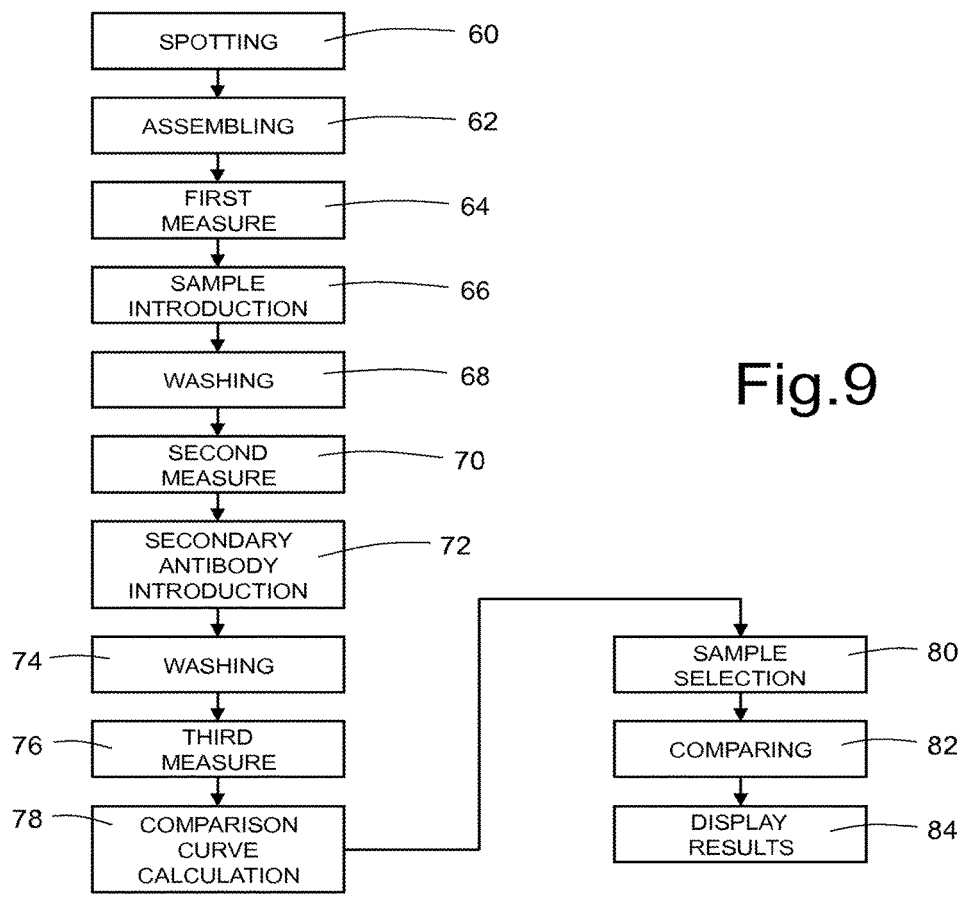
FIG. 9 is a flow-chart of an embodiment of the present method.

Initially, before mounting the microbalances 8 onto the body 2, step 60 of FIG. 9, a primary antibody 40 (e.g., the mouse anti-human TSH (anti-hTSH) 5405 SP-1 antibody) is deposited on the sensitive layers 22 of all microbalances 8A-E, using a spotting technique (functionalization step). This can be done as a manufacturing step, such that microbalances 8 specific for certain common tests are sold ready to use, or this can be done by the user, such that the same hardware can be used for any test.

Then, step 62, the microbalances 8 are assembled with the body 2 using the clips 4 or other fastening element, to obtain the concentration detecting device 1 of FIG. 1.

Thereafter, a calibration measurement is performed, without introducing liquids into the cells 5A-5E, step 64, generating five frequency values $f_{1A}$-$f_{1E}$, each one for a respective cell 5A-5E. Measuring may be performed as described in US 2010/0170324, above mentioned. The calibration measurement has the aim of allowing calibration and normalization of the concentration detecting device 1, with the frequency measure of the calibration cell 5A used for calibrating the other cells 5B-5E, to compensate for any manufacturing spread, and results of the measurements are stored for normalizing the following readings.

Then, reference samples 41A-41C and measure samples 41D-41E are introduced in the cells 5A-5E through input holes 10, e.g., using sample syringes 42, step 66. Of course, application of the sample(s) may be preceded by blocking buffer, as is typically performed in order to reduce non-specific binding to the antibodies.

Figure 4:
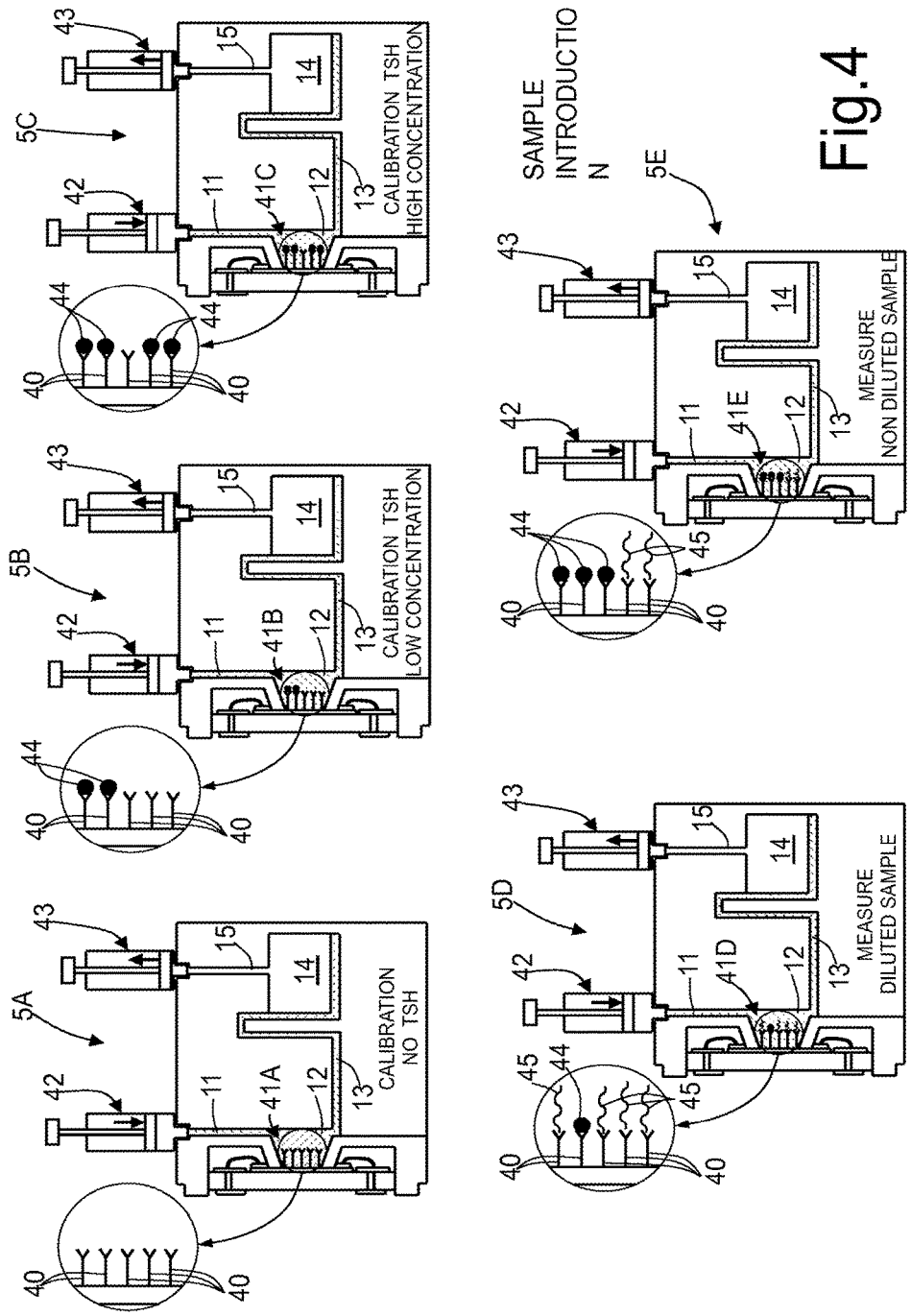
FIGS. 4-7 are representations of the cells of the device of FIG. 1, in subsequent steps of the present method.
Figure 5:
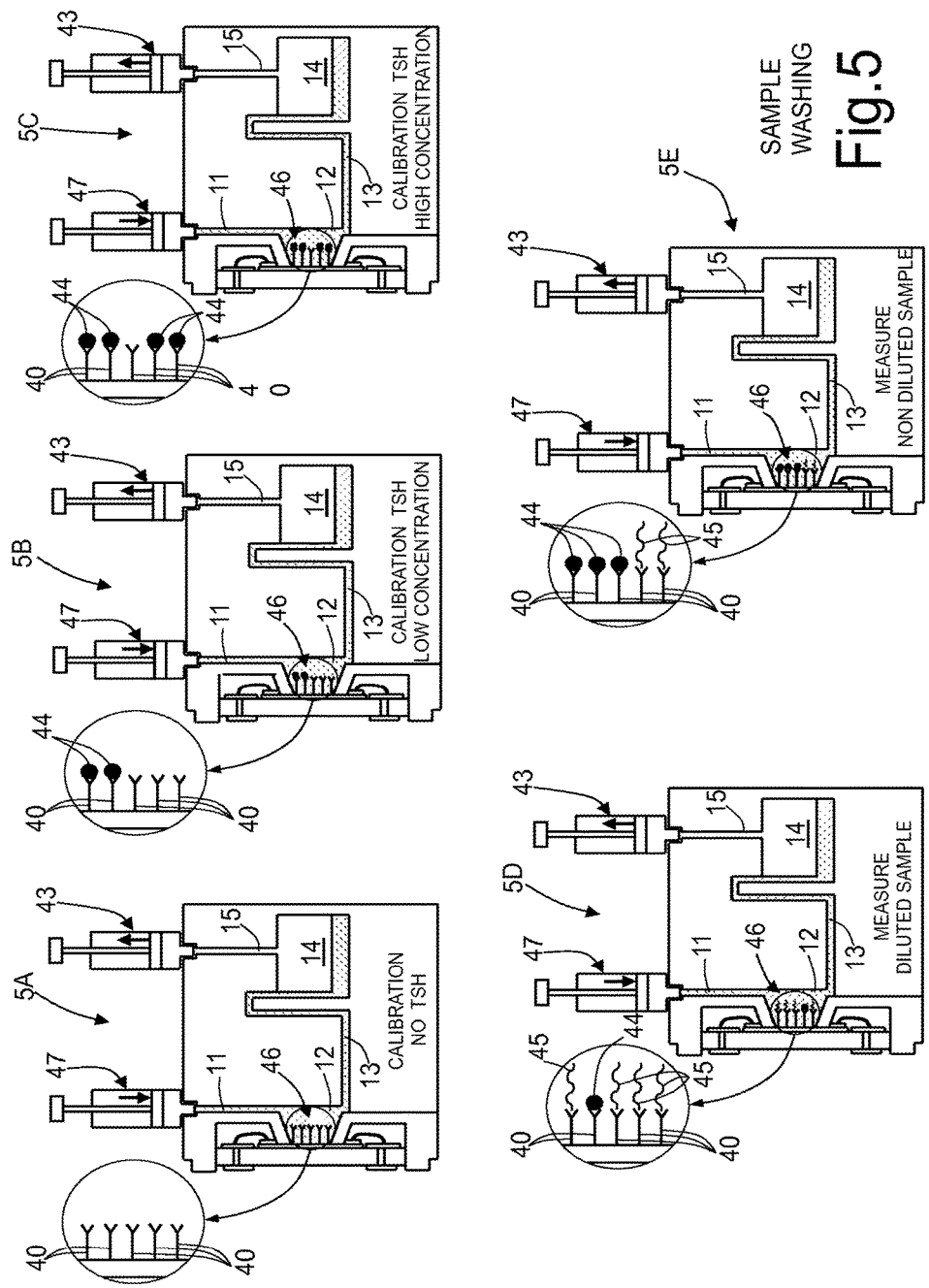

In detail, as shown in FIG. 4, calibration cell 5A is supplied with a blank sample 41A, including only a carrier liquid such as water or serum and/or buffer, as appropriate; first reference cell 5B is supplied with a first reference sample 41B, containing the carrier liquid and a known, low concentration of the target material 44; second reference cell 5C is supplied with a second reference sample 41C, containing the carrier liquid and a known, high concentration of the target material 44; the first measure cell 5D is supplied with a first measure sample 41D (sample to be analyzed, e.g., an organic liquid such as blood, urine, saliva or other biological sample) which has been diluted in a known manner (e.g., 1:4) and thus contains a unknown, low concentration of the target material 44. A second measure cell 5E is supplied with a second sample to be analyzed 41E, which is non-diluted or less diluted, and thus contains an unknown, high concentration of the target material 44. The target materials 44 in the first and second reference samples 41B, 41C may be synthetic ones or may be standard international samples of known concentration.

The sample syringes 42 may be actuated simultaneously by an external actuation system (not shown). The samples 41A-41E travel along the inlet conduits 11 and reach reaction chambers 12 of the respective cells 5A-5E. Here, TSH hormones 44 bind with the primary antibodies 40 before reaching the connection conduits 13 and then the disposal chambers 14, as shown in the enlarged details. The first and second measure samples 41D, 41E may also contain unwanted molecules 45 that have similar epitopes as TSH and may also bind with the primary antibodies 40 or may bind non-specifically to the sensitive layer of stack 22, as also shown in the enlarged details.

Transport of the samples 41A-41E along the conduits 11, 13 occurs partially by gravity, but may be helped by low pressure in the pumping conduits 15 generated by sucking pumps 43 connected to the venting holes 17, which are designed to prevent inadvertent backflow of fluids. In particular, sucking pumps 43 may be inactive during injection of the samples 41 and be actuated simultaneously for all cells 5 after a preset time, to allow the samples 41A-41E to remain in the reaction chambers 12 for a while, before being discharged to the waste chamber 14.

Next, step 68 (FIG. 5), a sample washing liquid 46 is introduced in the cells 5A-5E from inlet holes 10, e.g., using a first washing syringe 47. The sample washing liquid 46 may be any wash solution used in the art, and is typically buffered water and/or detergent. The wash solution for all cells 5 travels along conduits 11,13, reaction chamber 12 and is discharged into the discharge chamber 14. Again, the movement of the first washing liquid 46 may be helped by the sucking pumps 43. Washes can be repeated as needed.

Then, after drying of the reaction chambers 12, a second measurement is performed, step 70. The second measurement has the aim of detecting variations in the oscillation frequencies of the second to fifth microbalances 8B-8E due to the binding of the target materials 44 (and any unwanted molecules 45 that may remain) and generates five frequency values $f_{2A}$-$f_{2E}$ ($f_{2A}$ being used again for calibration). The results of the second measurements are also stored for subsequent use.

Figure 6:
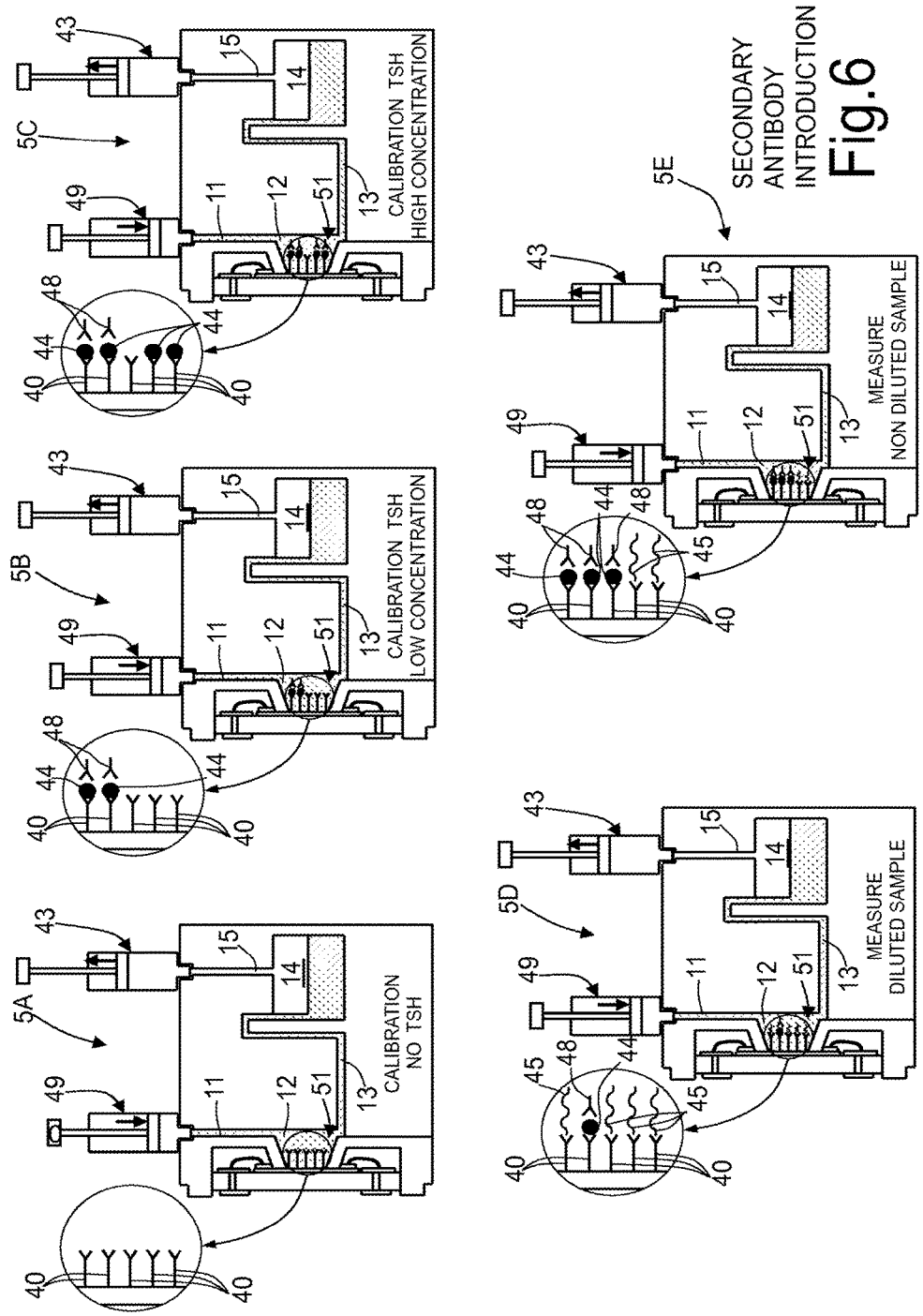

Thereafter, step 72 and FIG. 6, a secondary antibody 48 is introduced in cells 5B-5E through the input holes 10, e.g., by means of secondary antibody syringes 49. Also here, a blank sample without secondary antibody is introduced in the calibration cell 5A. The secondary antibody may be, e.g., mouse anti-hTSH 5409 SPTNE-5 secondary antibody or any anti-TSH antibody that preferably binds to a different epitope on TSH than the first antibody. Thus, the secondary antibody will preferentially bind only the target material 44 (e.g., TSH), but not the unwanted molecules 45. Also in this case, secondary antibody syringes 49 inject the secondary antibody 48 into the inlet conduits 11 and these reach reaction chambers 12 of the respective cells 5A-5E by gravity. After a while, the sucking pumps 43 may be actuated, to cause the non-reacted secondary antibodies 48 to be discharged into the discharge chamber 42.

Figure 7:
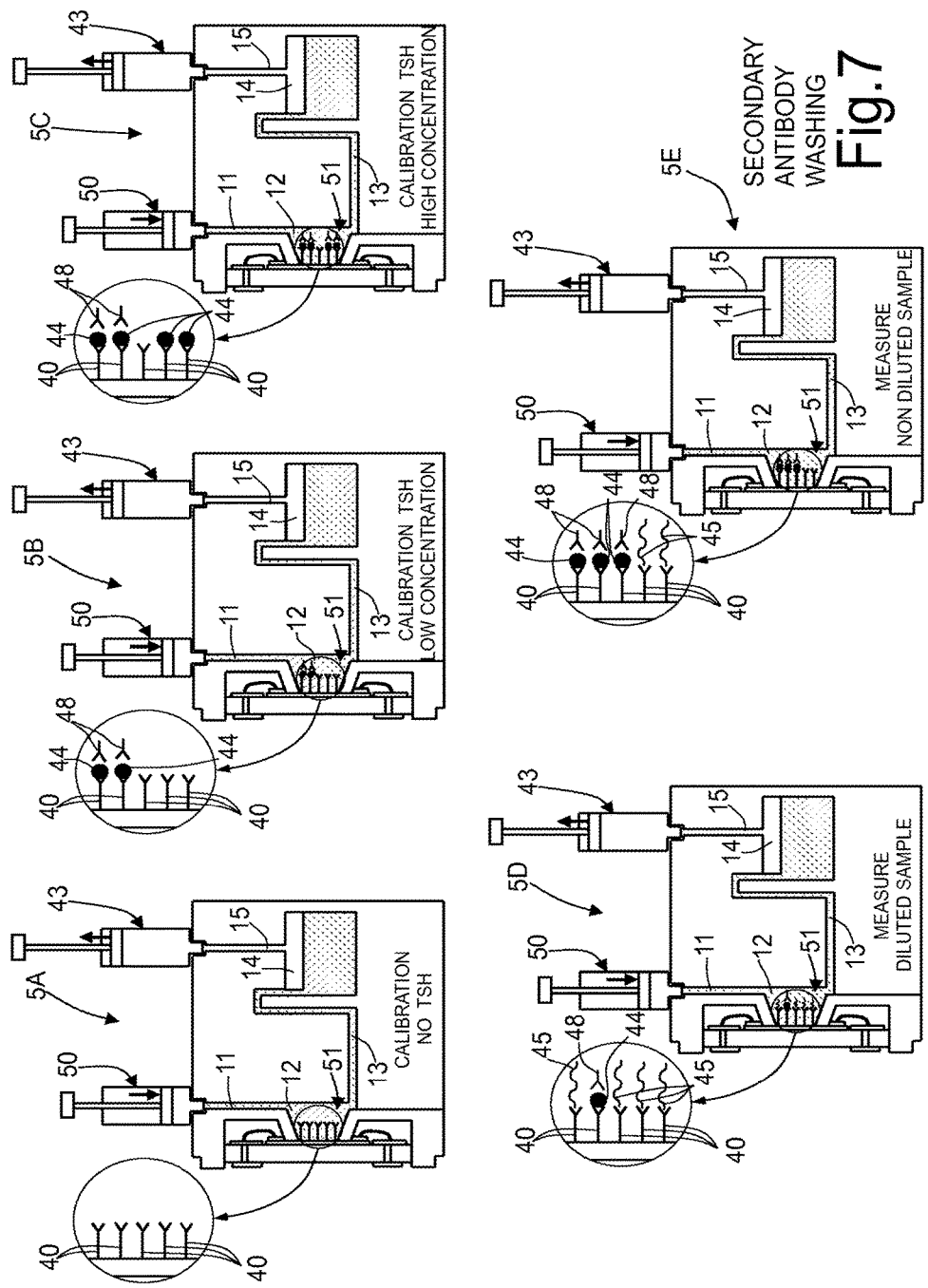

Next, step 74 and FIG. 7, a second washing liquid 51 is introduced in the cells 5A-5E from inlet holes 10, e.g., using a second washing syringe 50. The second washing liquid 51 may be the same as the first washing liquid or different and its movement may be helped by the sucking pumps 43. As above, washing steps can be repeated.

Then, after drying of the reaction chambers 12, a third measurement is performed, step 76. The third measurement has the aim of detecting variations of the oscillation frequencies of the second to fifth microbalances 8B-8E due to the binding of the target materials 44, the secondary antibody 48 (and any unwanted substances 45) and generates five frequency values $f_{3A}$-$f_{3E}$. The results of the third measurement are also stored for subsequent use.

Then, step 78, the differential frequencies (difference between the third and the second measured frequency values) are calculated for the reference and sample cells 5B-5E:

$$\Delta f_B = f_{3B} - f_{2B};$$

$$\Delta f_C = f_{3C} - f_{2C};$$

$$\Delta f_D = f_{3D} - f_{2D};$$

$$\Delta f_E = f_{3E} - f_{2E}.$$

The differential frequencies are directly related to the reacted quantity of the secondary antibody and thus to the quantity of the target material 44 in the various samples. In fact, since the second antibody does not react (or minimally reacts) with the unwanted molecules, the differential frequencies in the first and second sample cells are unaffected by any non-specific binding molecules.

Figure 8:
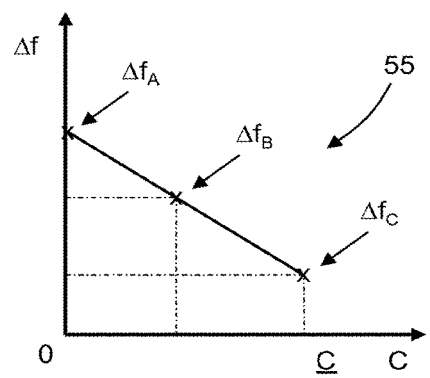
FIG. 8 is a measure curve used in this method.

Using the calibration frequency $f_A$, the differential reference frequencies $\Delta f_B$ and $\Delta f_C$, a reference curve 55 is obtained, as shown in FIG. 8, that shows on the abscissas the known quantity of the target material in the calibration cell 5A and in the first and second reference cells 5B, 5C and on the ordinates the relevant differential frequencies, step 78.

Then, step 80, the differential sample frequency $\Delta f_A$ or $\Delta f_E$ is selected to be compared with the reference curve 55. In fact, based on the specific concentration of the target material in the sample, one of the two readings may be out of scale or in a less precise portion of the curve. In particular, if the concentration of the target material is very high, the measure made using the non-diluted sample 41E may be higher than the second reference value $\Delta f_C$, where the calibration curve 55 is less reliable. In this case, the measure deriving from the diluted sample 41D (diluted differential frequency $\Delta f_D$) is used. On the contrary, in case of low concentration of the target material in the sample to be used, the diluted sample may have too low concentration of the target material. In this case, the reading from the diluted sample is disregarded, and the reading results from the non-diluted sample are used.

In general, by selecting a suitable level of dilution of the diluted sample 41D, one of the two differential frequency $\Delta f_D$ or $\Delta f_E$ is out of range, so the selection is made simply by comparing the differential sample frequencies $\Delta f_D$ and $\Delta f_E$ with the linear range of the calibration curve 55 (e.g., the range between $\Delta f_B$ and $\Delta f_C$) and discarding the differential sample frequency falling outside the allowable range.

Then, the sample concentration corresponding to the selected differential sample frequency is read from the calibration curve 55, step 82. In case the diluted differential frequency $\Delta f_D$ is used, the concentration value read from the calibration curve 55 is multiplied by the dilution ratio.

In the end, the detected concentration may be displayed or otherwise outputted or even stored for later use or processing, step 84.

Figure 10:
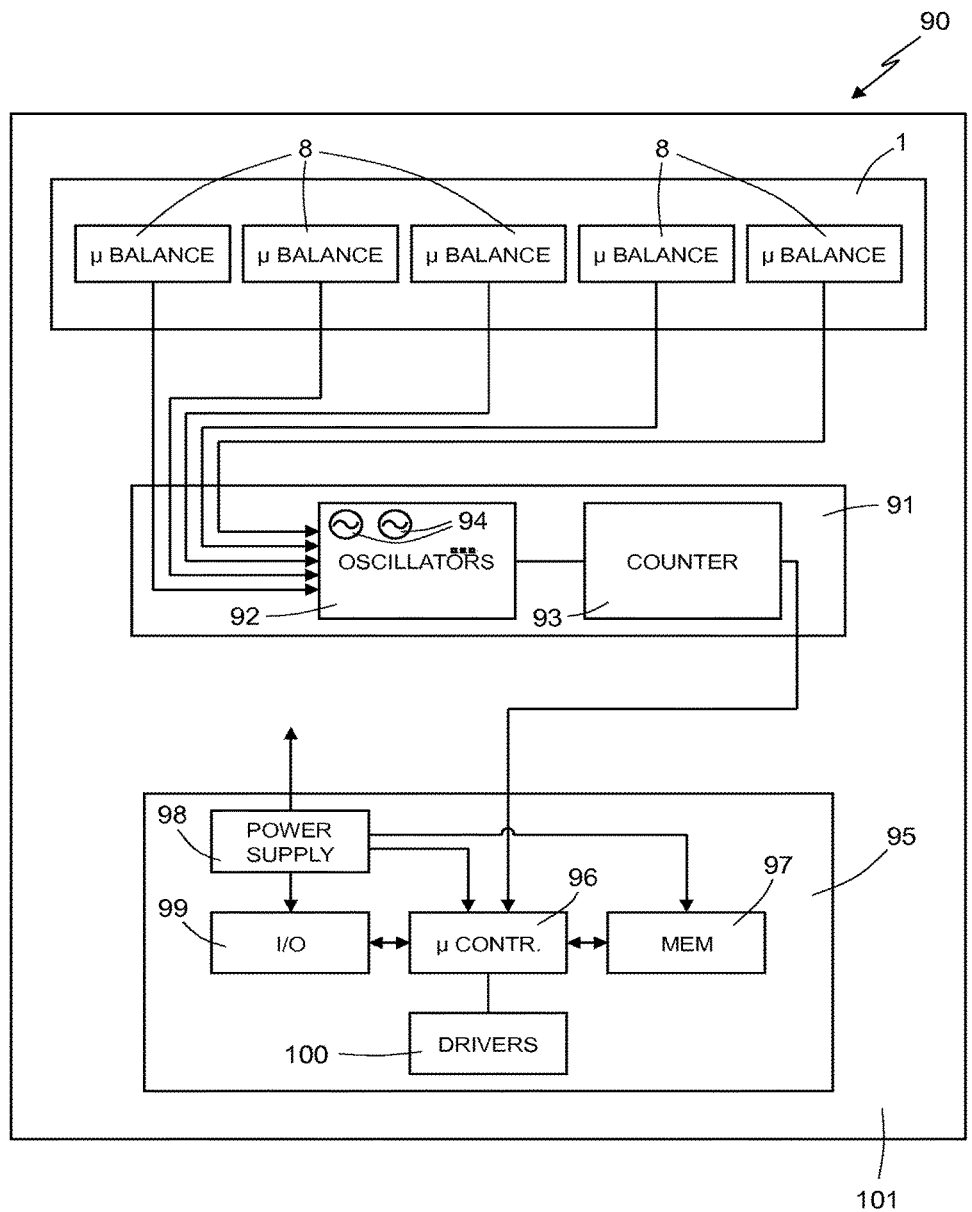
FIG. 10 shows an apparatus for measuring the concentration of biological materials.

The concentration detecting device 1 may be used in combination with a biochemical analysis apparatus 90 shown in FIG. 10, that receives the antibody cartridge described above, and provides the necessary electronics, fluidics, and the like to run the assay and report results.

The apparatus or driver 90 comprises the concentration detecting device 1 of FIG. 1 connected to an electronic unit 91, which includes an oscillator stage 92 and a converter 93, for example a counter. The oscillator stage 92 comprises a plurality of oscillators 94, one for each microbalance 8, and forms therewith a plurality of resonators, whose frequencies are the measured frequencies discussed with reference to FIGS. 4-9. In particular, the oscillator stage 92 drives the microbalances 8 and generates a plurality of periodic signals (pulse trains) having frequencies equal to the frequencies of the resonators. During the measuring steps 64, 70, and 76, the counter 93 counts the number N of pulses for each periodic signal within a fixed time interval T and generates digital signals that encode the measured frequencies. The oscillator stage 92 may be integrated with a single chip connected to all the microbalances 8 or be integrated separately for each microbalance 8 in a respective die 21.

The output of the electronic unit 91 is connected to a processing unit 95 comprising a microcontroller 96 connected to a memory 97, for example of an EEPROM type, to a power-supply stage 98, to an input/output stage 99, for example for displaying the results, and to a driver stage 100, for controlling automatic operation of the mechanical parts of the concentration detecting device 1, e.g., of the sucking pump 43. The microcontroller 96 thus acquires the frequency measurements, generates the reference curve 55, selects the differential sample frequency $\Delta f_D$ or $\Delta f_E$, compares the selected differential sample frequency with the reference curve and controls output of the final results.

The electronic unit 91 and the processing unit 95 may be housed in an external casing 101 that includes a recess (not shown) for inserting the concentration detecting device 1, electrical connectors (not shown) for connection to the microbalances 8 as well as mechanical parts coupled to the driving stage 100 and useful for the automatic or semiautomatic operation of the concentration detecting device 1, such as the syringes 42, 47, 49, 50, the sucking pump 43, an actuator for the sucking pump 43, valves, monitoring sensors and so on.

For example, the external casing may include light emitters and light receivers (not shown) to be arranged, e.g., on top of and below the body 2 for monitoring the presence and the travel of the liquids in the fluidic paths 9. In addition, the biochemical analysis apparatus 90 may include a temperature control module.

The concentration detecting device 1 allows the measure of the concentration of a target material, such as TSH, in an automatic manner, with delivery of all the reagents in a single component (body 2), after spotting the first antibody and assembling the multi-microbalance structure 3 onto the body 2. In fact, all subsequent operations (introductions of the samples and washing liquids, advancing of all the liquids in the fluidic paths, acquiring of the frequency measures and determination of the concentration) may be controlled in an automatic way by the biochemical analysis apparatus 90.

The concentration detecting device 1 is very sensitive and may measure a wide range of target material concentrations by including a diluted sample cell and non-diluted sample cell.

In fact, standard reference range for TSH is between 0.4 and 5 μIU/ml (wherein 1 μIU~0.5 ng), but values vary slightly from lab to lab and there is disagreement in the diagnostic community as to what constitute a normal reference range. The American Association of Clinical Endocrinologists (AACE) now recommends that doctors use 0.3 to 3.0 μIU/ml as a normal range.

Regardless, a microbalance may suitably have a sensitivity comprised between 0.03 μIU/ml (one tenth of the minimum normal value) and 30-50 μIU/ml (tenfold the maximum normal value) and that should be more than enough dynamic range for the assay.

The present device and method involve reactions that are the same as they occur in the human body; in fact, no chromophores, reagents or other extraneous matter are used, thus reliable results are obtained.

The discharged liquids are collected in the waste chamber 14 wherefrom they cannot exit, either back to the reaction chamber 12 or to the outside, by virtue of the winding shape of the discharge conduit 13; thus the device 1 reliably avoids any internal or external contamination.

The concentration detecting device 1 is of a single use type and forms a cartridge that can be inserted in the apparatus 90 and then disposed to be replaced by a new one for a further measuring operation. Its operation is very simple, may be controlled automatically and does not require manipulation by highly training lab technicians.

The calculation of the reference curve by measuring the variation of frequency of reference samples together with the measure samples inherently takes into account the efficiency of the reaction antigen-antibody.

Finally, it is clear that numerous modifications and variations may be made to the method and device described and illustrated herein, all falling within the scope of the invention, as defined in the attached claims. For example, the sucking pump 43 may be replaced by any other means, for example by a single external pump, for example a pump in the apparatus 90, connected to the venting holes 17.

In addition, although we have exemplified the device herein with TSH alone and using five cells, the cells can be multiplied, and the device arranged so as to detect one or more of TSH, T3, T4, and anti-thyroid microsomal antibodies—anti-thyroid peroxidase (anti-TPO), as medically determined to be appropriate in detecting various thyroid diseases. Furthermore, the device can easily be modified to detect any other biological material that is detectable by antibody.

The following reference is incorporated by reference herein in its entirety:

US 2010/0170324.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A disposable cartridge for an immunoassay, comprising:
a body including a first face, a second face continuous with and perpendicular to the first face, and a plurality of fluidic paths, each fluidic path including:
a respective inlet of a plurality of inlets at the second face;
a respective reaction chamber of a plurality of reaction chambers, the respective reaction chamber being fluidly coupled to the respective inlet of the fluidic path;
a respective disposal conduit of a plurality of disposal conduits, the respective disposal conduit being fluidly coupled to the respective reaction chamber of the fluidic path; and
a respective waste chamber of a plurality of waste chambers, the respective waste chamber being fluidly coupled to the respective disposal conduit of the fluidic path, the respective disposal conduit having a portion higher than at least one of said respective reaction chamber and said respective waste chamber of the fluid conduit, the portion of the respective disposal conduit being configured to prevent inadvertent fluid flow; and
a multi-microbalance structure mechanically coupled to the body and including a plurality of microbalances fluidly coupled to the fluidic path, respectively, each microbalance including:
a semiconductor diaphragm;
a stack of layers on the diaphragm and including a pair of electrodes, an outer sensitive layer, and a piezoelectric layer sandwiched between the pair of electrodes and the outer sensitive layer; and
an antibody bound to the outer sensitive layer, said sensitive layer facing a respective one of the reaction chambers.

2. The device of claim 1, wherein the plurality of fluidic paths and microbalances form a calibration cell.

3. The device of claim 2, wherein the plurality of fluidic paths and microbalances further form a sample cell and a reference cell.

4. The device of claim 1, wherein the plurality of inlets are configured to be coupled to a plurality of containers of a reference or sample liquid, respectively.

5. The device of claim 4, wherein the containers are syringes.

6. The device of claim 1, wherein the fluidic paths have the same shape.

7. The device of claim 6, further comprising a clip mechanically coupling the body and the multi-microbalance structure together.

8. The device of claim 1, wherein the second face includes a venting hole configured to be coupled to a vacuum source.

9. The device of claim 1, wherein each sensitive layer is configured to bind to a primary antibody for a target biological material.

10. A disposable cartridge for an immunoassay, comprising:
a body including a face and a plurality of fluidic paths, each fluidic path of the plurality of fluidic paths including:
an inlet at the face;
a reaction chamber fluidly coupled to the inlet;
a disposal conduit fluidly coupled to the reaction chamber; and
a waste chamber fluidly coupled to the disposal conduit, a portion of the disposal conduit being closer to the face than the reaction chamber, the waste chamber, or both; and
a multi-microbalance structure coupled to the body and including a plurality of microbalances, each microbalance of the plurality of microbalances fluidly coupled to a respective fluidic path, each microbalance including:
a diaphragm; and
a series of layers on the diaphragm, the series of layers including a pair of electrodes, a piezoelectric layer, and a sensitive layer having an antibody bound to a detection surface, the detection surface facing a respective one of the reaction chambers.

11. The disposable cartridge of claim 10, wherein the plurality of fluidic paths and microbalances form a calibration cell, a first sample cell, and a first reference cell.

12. The disposable cartridge of claim 11, wherein the plurality of fluidic paths and microbalances further form a second sample cell and a second reference cell.

13. The disposable cartridge of claim 10, wherein the inlet of each fluidic path is configured to be coupled to a syringe containing a liquid.

14. The disposable cartridge of claim 10, wherein the face includes a plurality of venting holes configured to be coupled to a vacuum source.

15. The disposable cartridge of claim 10, wherein the fluidic paths have the same shape.

16. A disposable cartridge for an immunoassay, comprising:
a body including a first face, a second face, and a plurality of fluidic paths, the plurality of fluidic paths forming a calibration cell, a first reference cell, and a first measure cell, each fluidic path having a same shape and including:
a respective inlet of a plurality of inlets in the second face;
a respective reaction chamber of a plurality of reaction chambers, the respective reaction chamber being in fluid communication with the respective inlet via a respective inlet conduit of a plurality of inlet conduits;
a respective disposal conduit of a plurality of disposal conduits, the respective disposal conduit being in fluid communication with the respective reaction chamber of the fluidic path; and
a respective waste chamber of a plurality of waste chambers, the respective waste chamber being in fluid communication with the respective disposal conduit of the fluidic path, the respective disposal conduit extending between the respective reaction chamber and the respective waste chamber, the respective disposal conduit having a portion that is closer to the second face than the respective reaction chamber and the respective waste chamber, the portion of the disposal conduit, in use, preventing inadvertent fluid flow; and
a multi-microbalance structure mechanically coupled to the body with a clip, the multi-microbalance structure including a plurality of microbalances, each microbalance being in fluid communication with the respective reaction chamber of a respective fluidic path, each microbalance including:
a respective semiconductor diaphragm on a die; and
a respective stack of layers on the semiconductor diaphragm and including a piezoelectric layer sandwiched between a pair of electrodes and an outer sensitive layer having antibodies bound to a detection surface, which faces a respective one of the reaction chambers.

17. The disposable cartridge of claim 16, wherein the plurality of fluidic paths further form a second reference cell and a second measure cell.

18. The disposable cartridge of claim 16, wherein the second face includes a plurality of venting holes that, in use, are coupled to a vacuum source.

19. The disposable cartridge of claim 16, wherein the plurality of inlets are, in use, coupled to a plurality of containers each containing a reference liquid or a sample liquid.

20. The disposable cartridge of claim 16, wherein the respective reaction chamber is formed, in part, by a respective microbalance.

* * * * *